United States Patent [19]

Brown et al.

[11] Patent Number: 6,048,816
[45] Date of Patent: Apr. 11, 2000

[54] CATALYST AND PROCESS FOR CONVERTING METHANOL TO HYDROCARBONS

[75] Inventors: Stephen Harold Brown, Princeton; Larry A. Green, Mickleton, both of N.J.; Mark Fischer Mathias, Pittsford, N.Y.; David H. Olson, Pennington, N.J.; Robert Adams Ware, Wyndmoor, Pa.; William A. Weber, Marlton, N.J.

[73] Assignee: Mobil Oil Corporation, Fairfax, Va.

[21] Appl. No.: 09/055,478

[22] Filed: Apr. 6, 1998

Related U.S. Application Data

[63] Continuation-in-part of application No. 08/725,277, Oct. 2, 1996, abandoned.

[51] Int. Cl.[7] ............................................... B01J 29/00
[52] U.S. Cl. ................................ 502/77; 502/60; 502/64; 502/71
[58] Field of Search ................................ 502/60, 64, 71, 502/77

[56] References Cited

U.S. PATENT DOCUMENTS

| | | | |
|---|---|---|---|
| 3,911,041 | 10/1975 | Kaeding et al. | 260/682 |
| 4,049,573 | 9/1977 | Kaeding | 252/432 |
| 4,088,706 | 5/1978 | Kaeding | 260/668 R |
| 4,480,145 | 10/1984 | Brennan et al. | 585/640 |
| 4,849,573 | 7/1989 | Kaeding | 585/640 |
| 5,171,921 | 12/1992 | Gaffney et al. | 585/653 |

*Primary Examiner*—Tom Dunn
*Attorney, Agent, or Firm*—Peter W. Roberts; Malcolm D. Keen

[57] ABSTRACT

There is provided a catalyst and a process for converting methanol or dimethyl ether to a product containing $C_2$ to $C_4$ olefins. The catalyst comprises a porous crystalline material having a Diffusion Parameter for 2,2-dimethylbutane of about 0.1–20 $sec^{-1}$ when measured at a temperature of 120° C. and a 2,2-dimethylbutane pressure of 60 torr (8 kPa). In addition, the catalyst is characterized by a hydrothermal stability such that, after steaming the catalyst at 1025° C. for 45 minutes in 1 atmosphere steam, the catalyst exhibits a methanol conversion activity of at least 50% when contacted with methanol at a methanol partial pressure of 1 atmosphere, a temperature of 430° C. and 0.5 WHSV. The porous crystalline material is preferably a medium-pore zeolite, particularly ZSM-5, which contains phosphorus and has been severely steamed at a temperature of at least 950° C.

6 Claims, 3 Drawing Sheets

CATALYST AND PROCESS FOR CONVERTING METHANOL TO HYDROCARBONS

RELATED APPLICATIONS

This application is a continuation-in-part of our U.S. application Ser. No. 08/725,277 filed Oct. 2, 1996, now abandoned, the entire disclosure of which is expressly incorporated herein by reference.

BACKGROUND TO THE INVENTION

The present invention relates to a catalyst and process for methanol and/or dimethyl ether to hydrocarbons, particularly light olefin rich in ethylene.

There is a growing need for light olefin, especially ethylene and propylene, for a variety of uses making it desirable to develop sources of the olefin additional to the conventional source, crude oil. One such additional source is methanol and/or dimethyl ether which can be catalytically converted over certain zeolite catalysts to olefin-containing hydrocarbon mixtures. For example, U.S. Pat. No. 3,911,041 discloses that methanol can be converted to $C_2$–$C_4$ olefin by contacting the methanol at a temperature of 300–700° C. with a crystalline aluminosilicate zeolite catalyst which has a Constraint Index of 1–12, such as ZSM-5, and which contains at least about 0.78% by weight of phosphorus incorporated in the crystal structure of the zeolite. U.S. Pat. No. 4,088,706 discloses that methanol can be converted to a hydrocarbon mixture rich in $C_2$–$C_3$ olefin and mononuclear aromatics, particularly p-xylene, by contacting the methanol with a crystalline aluminosilicate zeolite catalyst which has a Constraint Index of 1–12 and which has been modified by the addition of an oxide of boron or magnesium either alone or in combination or in further combination with oxide of phosphorus. U.S. Pat. No. 4,849,573 teaches that the use of zeolites with a Constraint Index of 1–12 and a silica to alumina molar ratio of 298 to 2000 increases the light olefin yield in the conversion of methanol to hydrocarbons.

U.S. Pat. Nos 4,049,573 and 4,088,706 disclose that modifying Constraint Index 1–12 zeolites, such as ZSM-5, with oxides of boron or magnesium, either alone or in combination with an oxide of phosphorus, increases the yield of p-xylene in the catalytic conversion of methanol to olefin and aromatics.

U.S. Pat. No. 4,480,145 discloses that the ethylene yield in the catalytic conversion of methanol over ZSM-5 can be increased by moderating the diffusivity of the zeolite by the use of the large crystal form of the zeolite and by silica "stuffing" of the zeolite pores. This patent also discloses that by steaming the zeolite at 180–820° C. to reduce its alpha activity to 6–10 the cycle life and methanol conversion activity of the zeolite can be increased.

However, none of the prior art catalysts exhibit the combination of ethylene selectivity and hydrothermal stability desirable in a commercial methanol conversion process, particularly a fluid bed process with continuous oxygen regeneration. According to the invention, it has now been found that certain porous crystalline materials having specific and closely-controlled diffusion characteristics, such as can be obtained by severe steaming of phosphorus-containing ZSM-5, exhibit unexpected hydrothermal stability and enhanced selectivity to $C_2$ to $C_4$ olefin, and particularly to ethylene, when used to convert methanol and/or dimethyl ether.

SUMMARY OF THE INVENTION

In one aspect, the invention resides in a catalyst for use in converting methanol or dimethyl ether to a product containing $C_2$ to $C_4$ olefin, the catalyst comprising a porous crystalline material having a Diffusion Parameter for 2,2-dimethylbutane of about 0.1–20 $sec^{-1}$ when measured at a temperature of 120° C. and a 2,2-dimethylbutane pressure of 60 torr (8 kPa) and being characterized by a hydrothermal stability such that, after steaming the catalyst at 1025° C. for 45 minutes in 1 atmosphere steam, the catalyst exhibits a methanol conversion activity of at least 50% when contacted with methanol at a methanol partial pressure of 1 atmosphere, a temperature of 430° C. and 0.5 WHSV.

Preferably, the porous crystalline material has a Diffusion Parameter of about 0.1–10 $sec^{-1}$ and most preferably about 0.2–5 $sec^{-1}$.

Preferably, the catalyst contains an oxide of phosphorus.

Preferably, the catalyst contains about 0.05 to about 20 wt %, and more preferably about 1 to about 10 wt %, of said oxide phosphorus on an elemental basis.

Preferably, the porous crystalline material is an aluminosilicate zeolite and most preferably is ZSM-5.

In a further aspect the invention resides in a process for converting methanol or dimethyl ether to a product containing $C_2$ to $C_4$ olefin over the catalyst according to said one aspect of the invention.

DETAILED DESCRIPTION OF THE INVENTION

The present invention provides a catalyst and its use in a process for selectively converting methanol or dimethyl ether to $C_2$–$C_4$ olefin, wherein the catalyst comprises a porous crystalline material having a Diffusion Parameter for 2,2-dimethylbutane of about 0.1–20 $sec^{-1}$, preferably 0.1–10 $sec^{-1}$ and most preferably 0.2–5 $sec^{-1}$, when measured at a temperature of 120° C. and a 2,2-dimethylbutane pressure of 60 torr (8 kPa).

As used herein, the Diffusion Parameter of a particular porous crystalline material is defined as $D/r^2 \times 10^6$, wherein D is the diffusion coefficient ($cm^2/sec$) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material employed in the process of the invention is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1–12, as measured on the zeolite alone without the introduction of modifiers and prior to any treatment to adjust the diffusivity of the catalyst. In addition to the medium-pore size aluminosilicate zeolites, other medium pore acidic metallosilicates, such as silicoaluminophosphates (SAPOs), can be used in the process of the invention.

Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. ZSM-48 and the conventional preparation thereof is taught by U.S. Pat. No. 4,375,573, the disclosure of which is incorporated herein by reference. MCM-22 is disclosed in U.S. Pat. Nos. 5,304,698 to Husain; 5,250,277 to Kresge et al.; 5,095,167 to Christensen; and 5,043,503 to Del Rossi et al., the disclosure of which patents are incorporated by reference.

Preferably, the zeolite employed in the process of the invention is ZSM-5 having a silica to alumina molar ratio of at least 250, as measured prior to any treatment of the zeolite to adjust its diffusivity.

The required diffusivity for the catalyst of present catalyst is between 0.1 and 20 $sec^{-1}$ and most typically will be between 0.2 and 5 $sec^{-1}$. Such a catalyst can be produced by severely steaming an intermediate pore zeolite as described above so as to effect a controlled reduction in the micropore volume of the catalyst to not less than 50%, and preferably to 50–90%, of that of the unsteamed catalyst. Reduction in micropore volume is derived by measuring the n-hexane adsorption capacity of the catalyst, before and after steaming, at 90° C. and 75 torr n-hexane pressure. Steaming of the porous crystalline material is effected at a temperature of at least about 850° C., preferably about 950 to about 1075° C., and most preferably about 1000 to about 1050° C. for about 10 minutes to about 10 hours, preferably from 30 minutes to 5 hours.

To effect the desired controlled reduction in micropore volume, it may be desirable to combine the porous crystalline material, prior to steaming, with a phosphorus modifier. The amount of phosphorus modifier, as measured on an elemental basis, may be between about 0.05 and about 20 wt. %, and preferably is between about 1 and about 10 wt. %, based on the weight of the final catalyst. Preferably, the atomic ratio of phosphorus to framework aluminum (i.e. in the zeolite framework) is no greater than 4 and more preferably from about 2 to about 4.

Incorporation of the phosphorus modifier into the catalyst of the invention is conveniently achieved by the methods described in U.S. Pat. Nos. 4,356,338, 5,110,776 and 5,231,064, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)_2PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3–5 hours.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt. % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20–200 microns.

The catalyst employed of the invention has a very low acid activity. Using the alpha test of acid activity disclosed in *Journal of Catalysis*, volume 61, page 395 (1980), the catalyst of the invention has an alpha value less than 10, preferably less than 5 and typically below 1 making the alpha test an unreliable indicia of the catalyst's performance. More specifically, the catalyst of the invention is characterized by an unusually high hydrothermal stability such that, after steaming the catalyst at 1025° C. for 45 minutes in 1 atmosphere steam, the catalyst exhibits a methanol conversion activity of at least 50% when contacted with methanol at a pressure of 1 atmosphere, a temperature of 430° C. and 0.5 WHSV, preferably at 1 WHSV and most preferably at 2 WHSV.

The process of the invention is preferably carried out in a moving or fluid catalyst bed with continuous oxidative regeneration. The extent of coke loading can then be continuously controlled by varying the severity and/or the frequency of regeneration.

The process of the present invention is conducted at a temperature of at least 300° C., preferably between about 350 and about 600° C., most preferably between about 360 and about 480° C., a pressure of between about 1 atmosphere and 1000 psig (100 and 7000 kPa), and a weight hourly space velocity of between about 0.1 and 1000. The feed to the process can be methanol, dimethyl ether, or a mixture of methanol and dimethyl ether either alone or in combination with other components. The process may be conducted in the presence of added hydrogen and/or added water such that the molar ratio of hydrogen and/or water to methanol in the feed is between about 0.01 and about 10.

The process of the invention converts methanol and/or dimethyl ether to a light olefin stream in which ethylene comprises over 30 wt %, and typically over 40 wt %, of the $C_2$ to $C_4$ olefin and in which ethylene comprises more than 90 wt %, and preferably more than 95 wt %, of the $C_2$ component.

The invention will now be more particularly described with reference to the following Examples and the accompanying drawings in which.

In the Examples, micropore volume (n-hexane) measurements were made on a computer controlled (Vista/Fortran) duPont 951 Thermalgravimetric analyzer. Isotherms were measured at 90° C. and adsorption values taken at 75 torr n-hexane. The diffusion measurements were made on a TA Instruments 2950 Thermalgravimetric Analyzer equipped with a Thermal Analysis 2000 controller, a gas switching accessory and an automatic sample changer. Diffusion measurements were made at 120° C. and 60 torr 2,2-dimethylbutane and data were plotted as uptake versus square root of time. Fixed bed catalytic testing was conducted using a ⅜" (1 cm) outside diameter, down-flow reactor equipped with a thermocouple. Methanol and water were all pumped to the reactor by way of a vaporizer equipped with a static mixer to thoroughly gasify and mix the feedstocks upstream of the reactor. The reactor was equipped with a back pressure regulator to enable examination of the products at a wide variety of temperature, pressures and WHSV's. The total reactor effluent was analyzed, on line, by gas chromatography. Methanol conversion was calculated based on hydrocarbon formation only. Selectivities to hydrocarbon product were calculated on a "water free" basis.

EXAMPLE 1

Figure 1:
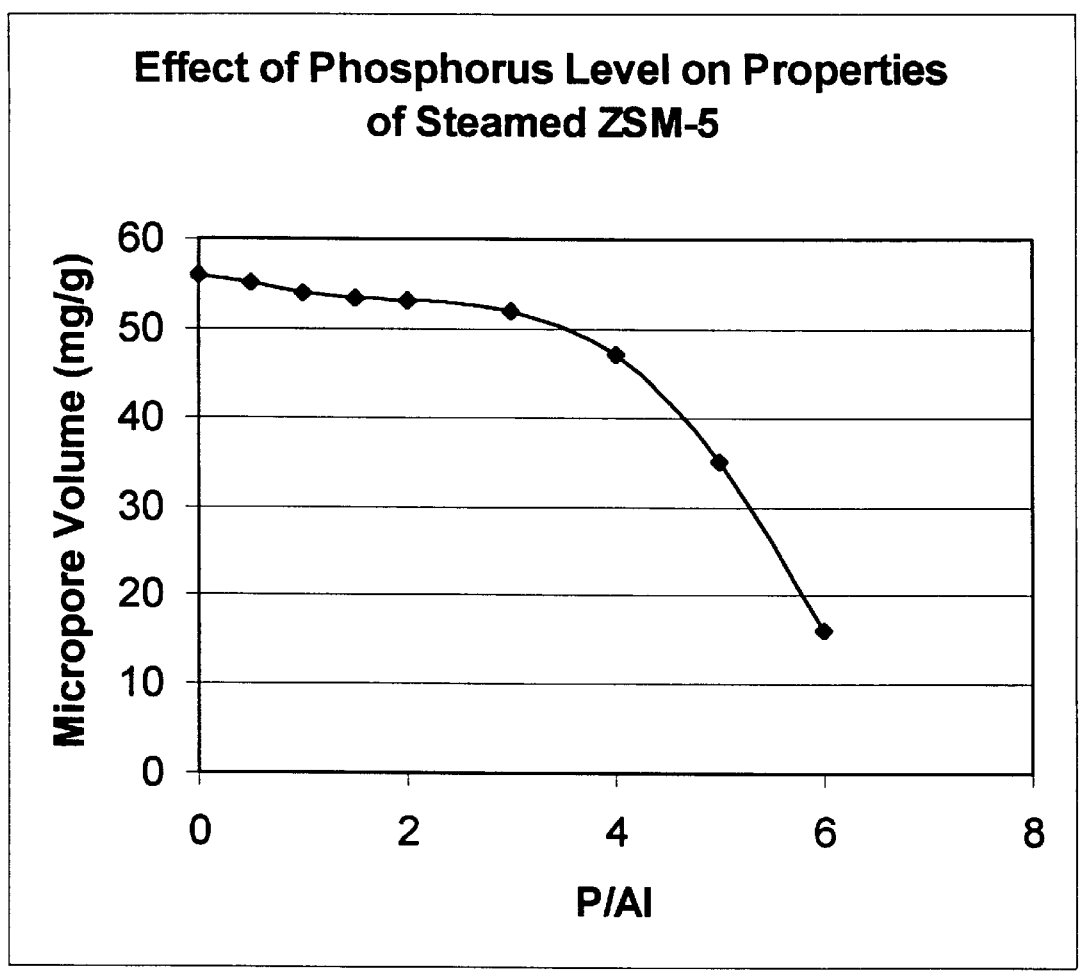
FIG. 1 is a graph of n-hexane sorption against phosphorus/framework aluminium atomic ratio for the catalysts of Example 1.

Catalysts were prepared from silica-bound ZSM-5 (65 wt % zeolite, silica:alumina molar ratio of 450:1) by treating the zeolite catalyst with different aqueous $H_3PO_4$ solutions having different amounts of $H_3PO_4$ followed by air calcination at 540° C. for 2 hours. The nominal phosphorus/aluminum atomic ratio, where the ratio is based on the framework aluminum content of the catalyst, characterizing each of the catalysts was between 0 and 6. Each catalyst was subsequently steamed for 4 hours at 1025° C. Then the amount of n-hexane sorbed by the catalyst was measured. The results are shown in FIG. 1. Because n-hexane sorption is a good test of crystallinity, the results clearly show that the stability of the catalyst decreases with increasing P/Al.

EXAMPLE 2

Figure 2:
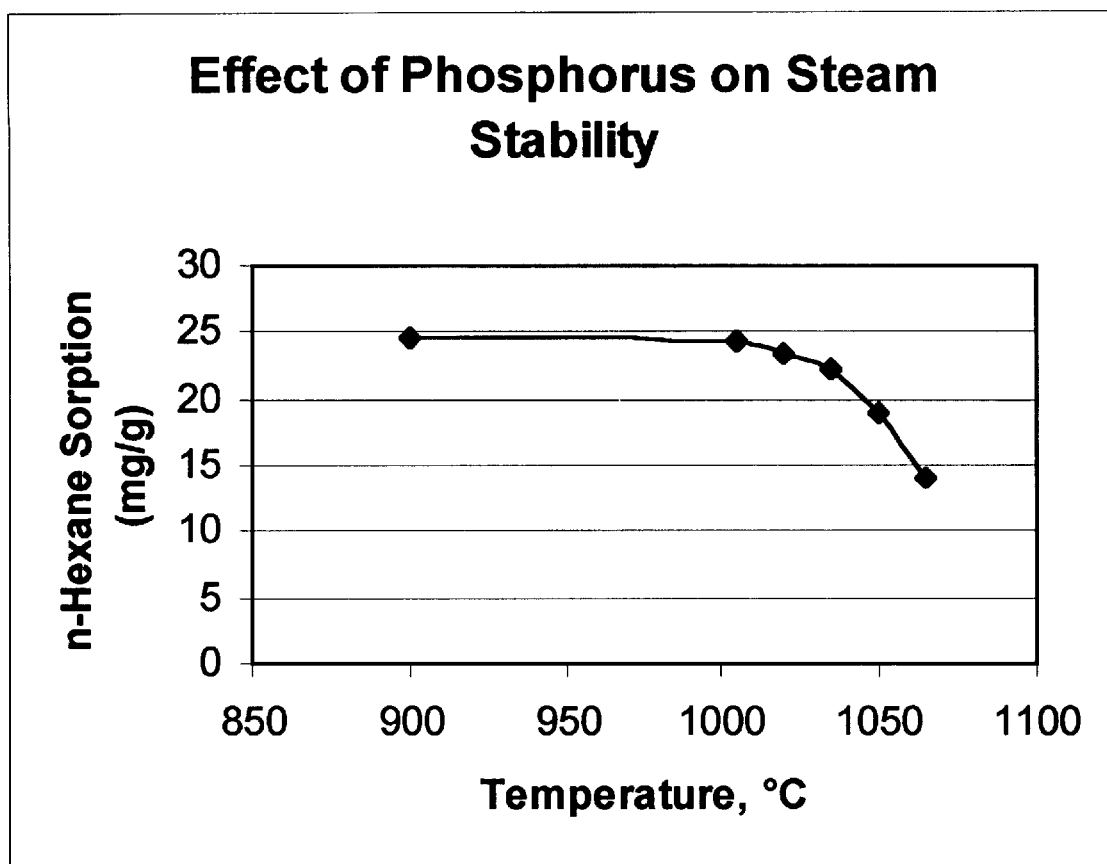
FIG. 2 is a graph of n-hexane sorption against steaming temperature for catalyst of Example 2.
Figure 3:
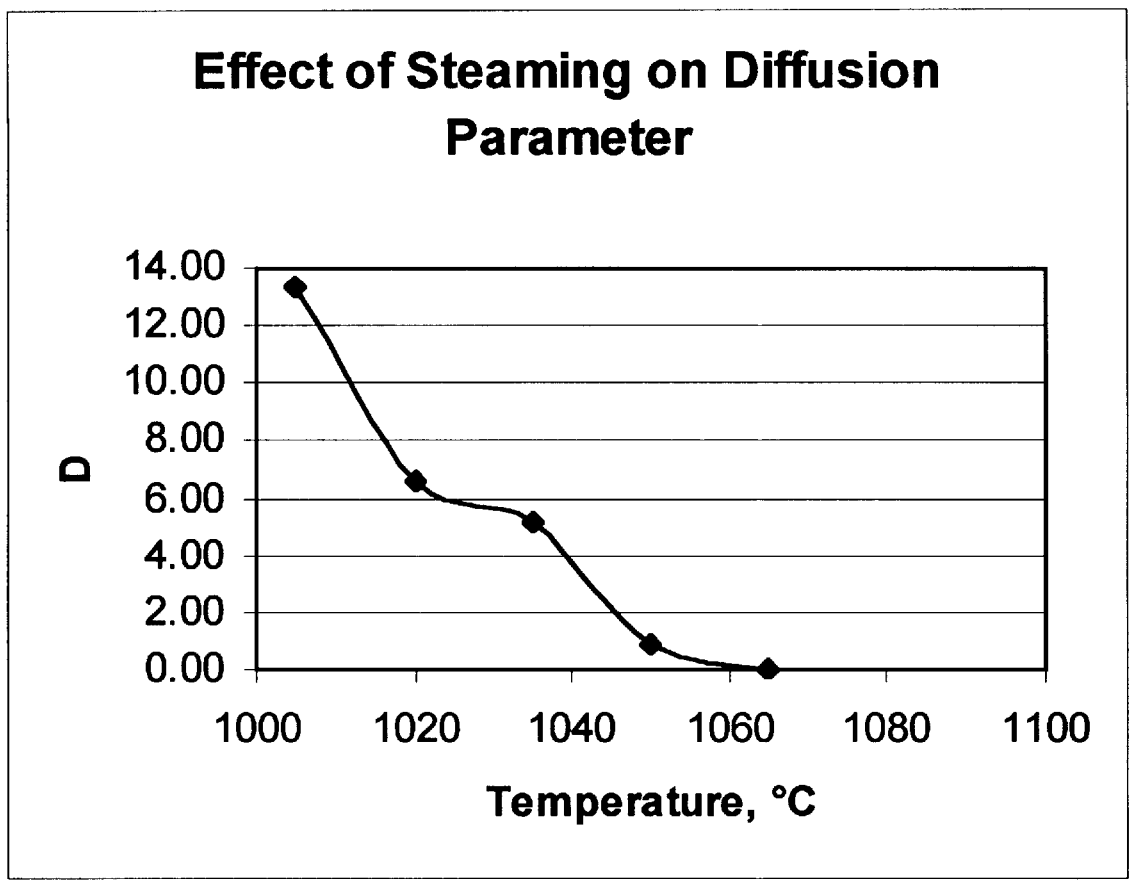
FIG. 3 is a graph of Diffusion Parameter against steaming temperature for catalyst of Example 2.

A catalyst was prepared containing 25 wt % ZSM-5 (silica/alumina molar ratio of 450) and about 4.5 wt % phosphorus in a kaolin clay binder by treating the clay-bound zeolite with aqueous $H_3PO_4$ solution followed by air calcination at 540° C. for 2 hours. The catalyst had an n-hexane sorption of 25 mg/g and a Diffusion Parameter of about 34 $sec^{-1}$. The catalyst was subsequently steamed for 1 hour at various temperatures between 900 and 1065° C. Following each steam treatment the catalyst n-hexane sorption and the diffusion parameter, D, were measured. The results are shown in FIGS. 2 and 3. FIG. 2 demonstrates that the phosphorus stabilized catalysts are structurally stable to about 1050° C. FIG. 3 shows that the value of the diffusion parameter, D, decreases with increasing temperature.

EXAMPLE 3

Phosphoric acid, kaolin clay, and 450:1 $SiO_2/Al_2O_3$ ZSM-5 were slurried in water and spray dried to make a typical fluid-bed catalyst. The catalyst was calcined in air at 510° C. The finished catalyst contained 40 wt % ZSM-5 and 4.5 wt % phosphorus. This material had an n-hexane sorption of 33.5, a diffusion parameter of 27, and an alpha of about 7.

The catalyst was steamed at 1 atmosphere and 1050° C. for 45 minutes and the resulting material had an n-hexane sorption of 31 mg/g and a diffusion parameter of 0.5.

The steamed catalyst was subjected to a further steaming at 1 atmosphere and 1025° C. for 45 minutes and then tested for methanol conversion activity. At 1 WHSV and 430° C. the catalyst converted 97% of the feedstock methanol to hydrocarbon product.

EXAMPLE 4

Large crystal NH4ZSM-5 zeolite having a crystal size of about 2 microns was extruded into 1/16 inch extrudates comprising 65 wt % ZSM-5 and 35 wt % alumina. The catalyst was calcined in air at 550° C. to obtain the hydrogen form and then divided into thre portions. The first portion was steamed at 1 atm and 510° C. for 1 hour and the resultant catalyst had an n-hexane sorption of 79 mg/gm, a diffusion parameter of 12 and an alpha of 200. The second portion of catalyst was steamed at 1 atm and 675° C. for 1 hour and the resultant catalyst has an n-hexane sorption of 74, a diffusion parameter of 10 and an alpha of 15. The two catalysts were tested for methanol conversion and performed as disclosed in U.S. Pat. No. 4,480,145.

The third portion of the catalyst was steamed at 1 atm steam and 870° C. for 1 hour and 0.5 gm of the steamed catalyst was tested for methanol conversion activity. At 1 WHSV and 430° C., the catalyst converted 30% of the feedstock methanol to hydrocarbon product. It will be appreciated that steaming at 870° C. for 1 hr is a less severe steaming than 1025° C. for 45 minutes. The catalyst of this Example would be expected to convert less than 5% of the methanol to hydrocarbons after steaming at 1025° C. for 45 minutes.

EXAMPLE 5 COMPARATIVE

Boron, magnesium, and lanthanum containing ZSM-5's were prepared as follows. A base microsphere was obtained by spray-drying a mixture of 450:1 ZSM-5, kaolin clay, and silica. After a rotary calcination at about 550° C., the final composition was 40 wt % ZSM-5A, 30 wt % silica, and 30 wt % kaolin.

Separate batches of the catalyst were impregnated by incipient wetness with: (1) Boron solution—20 gm boric acid; 80 gm distilled water; 8 gm 30 wt % ammonium hydroxide, (2) Magnesium solution—20 gm magnesium nitrate hexahydrate; 80 gm water, and (3) Lanthanum solution—20 gm lanthanum nitrate hexahydrate; 80 gm water.

After impregnation, the catalysts were first dried for 2 hours at 150° C. followed by a 4 hour calcination in air at 550° C. to convert the ammonium and nitrate salts to oxides. This resulted in the production of 3 catalysts with the following elemental loadings of magnesium, lanthanum, and boron:

Catalyst 1—0.2 wt % boron,

Catalyst 2—0.5 wt % magnesium, and

Catalyst 3—4.9 wt % lanthanum.

Catalyst synthesis was completed by calcination at 1000° C. in 1 atmosphere steam. After steaming, Catalyst 3 containing 4.9 wt % lanthanum had an n-hexane sorption of 31 and a diffusion parameter of 1.4, whereas Catalyst 1 containing 0.2 % boron had an n-hexane sorption of 33 and a diffusion parameter of 2.6.

The steamed catalysts were then tested for methanol conversion activity. At 0.5 methanol WHSV and 430° C., Catalyst 3 converted 2% of the feedstock methanol to hydrocarbon product, whereas Catalyst 1 converted 10% of the feedstock methanol to hydrocarbon product.

What is claimed is:

1. A catalyst for use in converting methanol or dimethyl ether to a product containing $C_2$ to $C_4$ olefins, the catalyst comprising a porous crystalline material having a Diffusion Parameter for 2,2-dimethylbutane of about 0.1–20 $sec^{-1}$ when measured at a temperature of 120° C. and a 2,2-dimethylbutane pressure of 60 torr (8 kPa) and being characterized by a hydrothermal stability such that, after steaming the catalyst at 1025° C. for 45 minutes in 1 atmosphere steam, the catalyst exhibits a methanol conversion activity of at least 50% when contacted with methanol at a methanol partial pressure of 1 atmosphere, a temperature of 430° C. and 0.5 WHSV.

2. The catalyst of claim 1, wherein said Diffusion Parameter of said porous crystalline material is about 0.2–5 $sec^{-1}$.

3. The catalyst of claim 1 and containing an oxide of phosphorus.

4. The catalyst of claim 1 and containing about 0.05 to about 20 wt % of an oxide of phosphorus on an elemental basis.

5. The catalyst of claim 1, wherein the porous crystalline material is an aluminosilicate zeolite.

6. The catalyst of claim 5 wherein said zeolite is ZSM-5 or ZSM-11.

\* \* \* \* \*